(12) United States Patent
Fessmann et al.

(10) Patent No.: US 7,056,354 B2
(45) Date of Patent: Jun. 6, 2006

(54) COMPOUNDS DERIVED FROM DIAMINOPYRAZOLE SUBSTITUTED BY A HETEROAROMATIC RADICAL AND THEIR USE IN OXIDATION DYEING OF KERATINOUS FIBERS

(75) Inventors: Thilo Fessmann, Aulnay-sous-Bois (FR); Eric Terranova, Magagnosc (FR)

(73) Assignee: L'Oreal, Paris (FR)

( * ) Notice: Subject to any disclaimer, the term of this patent is extended or adjusted under 35 U.S.C. 154(b) by 56 days.

(21) Appl. No.: 10/484,054

(22) PCT Filed: Jul. 9, 2002

(86) PCT No.: PCT/FR02/02397

§ 371 (c)(1),
(2), (4) Date: Jul. 30, 2004

(87) PCT Pub. No.: WO03/008405

PCT Pub. Date: Jan. 30, 2003

(65) Prior Publication Data

US 2004/0255397 A1    Dec. 23, 2004

(30) Foreign Application Priority Data

Jul. 18, 2001    (FR)    ................................ 01 09622

(51) Int. Cl.
*A61K 7/13*    (2006.01)

(52) U.S. Cl. .................. 8/405; 8/406; 8/409; 8/410; 8/411; 8/412; 8/423; 8/568; 8/570; 8/579; 548/302.7

(58) Field of Classification Search ................... 8/405, 8/406, 409, 410, 411, 412, 423, 568, 570, 8/579; 548/302.7
See application file for complete search history.

(56) References Cited

U.S. PATENT DOCUMENTS 5,061,289 A    10/1991    Clausen et al. ................ 8/405
5,865,855 A *   2/1999    Doehling et al. .............. 8/409

FOREIGN PATENT DOCUMENTS

DE    19730412    12/1998
EP    375977    7/1990

OTHER PUBLICATIONS

STIC Search Report dated Jan. 5, 2005.*

* cited by examiner

*Primary Examiner*—Eisa Elhilo
(74) *Attorney, Agent, or Firm*—Fulbright & Jaworski L.L.P.

(57) ABSTRACT

The invention concerns compounds derived from diaminopyrazole of formula (I), wherein: Ar is a 5- or 6-membered heteroaromatic radical capable of being condensed with one or several heteroaromatic cycles each comprising 5 or 6 members, and their physiologically acceptable addition salts with and acid. The invention also concerns compositions containing such a compound for oxidation dyeing of keratinous fibers and the method using said compositions

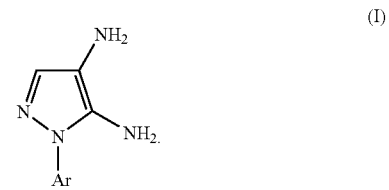

(I)

29 Claims, No Drawings

COMPOUNDS DERIVED FROM DIAMINOPYRAZOLE SUBSTITUTED BY A HETEROAROMATIC RADICAL AND THEIR USE IN OXIDATION DYEING OF KERATINOUS FIBERS

This application is a U.S. national phase application under 35 U.S.C. § 371 of International Application No. PCT/FR02/02397 filed 9 Jul. 2002, which claims priority to French Application No. 01/09622 filed 18 Jul. 2001, the entire disclosures of which are incorporated herein by reference.

The present invention relates to novel compounds derived from diaminopyrazole, to a composition for the oxidation dyeing of keratin fibers, and in particular of human keratin fibers such as the hair, comprising at least one compound derived from diaminopyrazole as oxidation base, and to the oxidation dyeing processes using it.

It is known practice to dye keratin fibers, and in particular human hair, with dye compositions containing oxidation dye precursors, in particular ortho- or para-phenylenediamines, ortho-aminophenols or para-aminophenols and heterocyclic compounds such as diaminopyrazole derivatives, which are generally referred to as oxidation bases. The oxidation dye precursors, or oxidation bases, are colorless or weakly colored compounds which, when combined with oxidizing products, can give rise to colored compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers makes it possible to obtain a wide range of colors.

The so-called "permanent" coloration obtained by means of these oxidation dyes must moreover satisfy a certain number of requirements. Thus, it must have no toxicological drawbacks and it must allow shades of the desired strength to be obtained and have good resistance to external agents (light, bad weather, washing, permanent-waving, perspiration and friction).

The dyes must also allow white hairs to be covered, and, lastly, they must be as unselective as possible, i.e. they must allow the smallest possible differences in coloration to be produced over the entire length of the same keratin fiber, which may indeed be differently sensitized (i.e. damaged) between its tip and its root. They must also show good chemical stability in the formulations, and must have a good toxicological profile.

Furthermore, for a certain number of applications, dyes that produce chromatic shades on the hair are desired.

Patent application EP 375 977 discloses 4,5-diaminopyrazole derivatives of use as coloring agents in oxidation dyeing.

Application DE 197 30 412 also discloses compounds of azabispyrazole type which can be used as direct dyes in the range of the reds.

However, these dyes do not satisfy all the above requirements.

The Applicant has now discovered, entirely surprisingly and unexpectedly, that it is possible to obtain dyes, which are capable of producing powerful, particularly chromatic, bright and relatively unselective colorations, which have excellent properties of resistance to the various attacking factors to which keratin fibers may be subjected, by using as oxidation base the diaminopyrazoles of the formula (I) below or physiologically acceptable salts thereof.

One subject of the present invention is thus a compound derived from diaminopyrazole of formula (I):

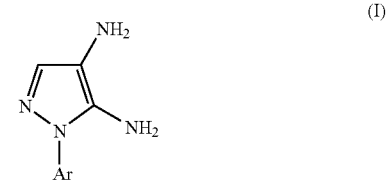

in which Ar is a 5- or 6-membered heteroaromatic radical which can be condensed with one or more aromatic or heteroaromatic rings, each comprising 5 or 6 ring members.

Another subject of the invention is a compound of formula (I), characterized in that Ar is optionally substituted by at least one radical chosen from linear or branched $C_1$ to $C_6$ alkyl radicals, linear or branched $C_1$ to $C_6$ alkoxy radicals, linear or branched $C_1$ to $C_6$ mono- or polyaminoalkyl radicals, linear or branched $C_1$ to $C_6$ mono- or polyhydroxyalkyl radicals, amino, hydroxyl, F, Cl, Br, I, trifluoromethyl, CHO, $CO_2H$, $CO_2Me$, $CO_2Et$, $CONH_2$, $CONHR_1$, $CON(R_1)_2$, $SO_3H$, $SO_2NH_2$, $SO_2Me$ or piperazinyl radicals, or phenyl radicals optionally substituted by at least one radical chosen from linear or branched $C_1$ to $C_6$ alkyl radicals, linear or branched $C_1$ to $C_6$ alkoxy radicals, linear or branched $C_1$ to $C_6$ mono- or polyaminoalkyl radicals, linear or branched $C_1$ to $C_6$ mono- or polyhydroxyalkyl radicals or amino, hydroxyl, F, Cl, Br, I, trifluoromethyl, CHO, $CO_2H$, $CO_2Me$, $CO_2Et$, $CONH_2$, $SO_3H$, $SO_2NH_2$, $SO_2N(R_1)_2$ or $SO_2Me$ radicals, $R_1$ being chosen from linear or branched $C_1$ to $C_6$ alkyl radicals, linear or branched $C_1$ to $C_6$ mono- or polyaminoalkyl radicals, linear or branched $C_1$ to $C_6$ mono- or polyhydroxyalkyl radicals, or trifluoromethyl, CHO, $CO_2Me$, $CO_2Et$, $CONH_2$, $SO_3H$, $SO_2NH_2$ or $SO_2Me$ radicals, and physiologically acceptable salts thereof.

Preferably, $R_1$ will be chosen from $C_1$ to $C_4$ alkyl derivatives.

The term "5- or 6-membered heteroaromatic" is understood to mean, within the meaning of the present application, an aromatic nucleus formed of 5 or 6 atoms, at least one of which is a heteroatom chosen from the group formed by N, O and S.

It will preferably be a radical chosen from the pyridinyl, pyrazinyl, pyrimidinyl, pyridazinyl, pyrrolyl, imidazolyl, pyrazolyl, furanyl, thiophenyl, triazolyl or triazinyl radicals. More preferably still, it will be a pyridinyl radical.

The term "radical condensed with one or more aromatic or heteroaromatic rings, each comprising 5 or 6 ring members" is understood to mean, within the meaning of the present application, a radical comprising 2 or 3 aromatic or heteroaromatic rings such that at least two carbon atoms of said radical are common to at least 2 of said aromatic or heterocyclic rings.

It will preferably be a radical chosen from the naphthyl, azanaphthyl, diazanaphthyl, triazanaphthyl or tetraazanaphthyl radicals, such as the quinolinyl, isoquinolinyl, oxyisoquinolinyl, quinoxalinyl or naphthyridinyl radicals; or the acridinyl, pyrazolo-[3,4-b]pyridinyl, pyrazolo[3,4-c]pyridazinyl or thieno-[3,2-c]pyridinyl radicals.

A subject of the invention is also the physiologically acceptable acid salts of the compounds of formula (I), such as the hydrochlorides, hydrobromides, sulfates, tartrates, lactates or acetates.

A subject of the invention is also a composition for the oxidation dyeing of keratin fibers, and in particular of human keratin fibers such as the hair, characterized in that it contains, in a medium that is suitable for dyeing, as oxidation base, at least one diaminopyrazole of formula (I) above, or physiologically acceptable acid salts thereof.

As mentioned above, the colorations obtained with the oxidation dye composition in accordance with the invention are powerful, particularly bright and chromatic. They in particular produce red shades that are free of or contain very little blue or yellow. Furthermore, they show excellent properties of resistance with respect to the action of various external agents (light, bad weather, washing, permanent-waving, perspiration and friction).

A subject of the invention is also a process for the oxidation dyeing of keratin fibers using such a dye composition.

As examples of diaminopyrazoles of formula (I) according to the invention, mention may be made of the compounds belonging to the following classes:

1) Pyridine Series

| Structure | Name | Structure | Name | Structure | Name |
|---|---|---|---|---|---|
| [structure] | 2-Pyridin-2-yl-2H pyrazole-3,4-diamine | [structure] | 2-Isoquinolin-1-yl-2H-pyrazole-3,4-diamine | [structure] | 2-(6-Methyl-4-trifluoro-methyl-pyridin-2-yl)-2H-pyrazole-3,4-diamine |
| [structure] | 2-(6-Chloro-4-trifluoro-methyl-pyridin-2-yl)-2H pyrazole-3,4-diamine | [structure] | 2-(5-Chloro-3,6-bis trifluoro-methyl-1-pyridin-2-yl)-2H pyrazole-3,4-diamine | [structure] | 2-(1,3,4-Trimethyl-1H-pyrazolo[3,4-b]pyridin-6-yl)-2H-pyrazole-3,4-diamine |
| [structure] | 2-(3-Amino-pyridin-2-yl)-2H-pyrazole-3,4-diamine | [structure] | 2-(5-Amino-pyridin-2-yl)-2H-pyrazole-3,4-diamine | [structure] | 2-(5,7-Bis trifluoro methyl [1,8] naphth yridin-2-yl)-2H-pyrazole-3,diamine |
| [structure] | 2-(2-Oxy-isoquino-lin-3-yl)-2H-pyrazole-3,4-diamine | [structure] | 2-(3-Amino-4-methyl-1H-pyrzolo[3,4-b]pyridin-6-yl)-2H-pyrazole-3,4-diamine | [structure] | 2-(6-Fluoro-pyridin-2-yl)2H-pyrazole-3,4-4-diamine |

-continued

| Structure | Name | Structure | Name | Structure | Name |
|---|---|---|---|---|---|
| 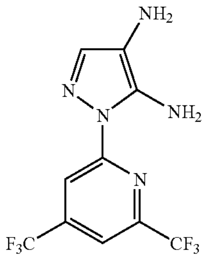 | 2-(4,6-Bis-trifluoromethyl-pyridin-2-yl)-2H-pyrazole-3,4-diamine | 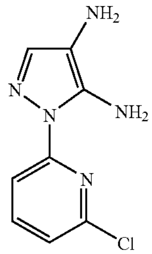 | 2-(6-Chloro-pyridin-2-yl)-2H-pyrazole-1,4-diamine | 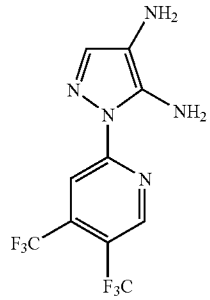 | 2-(4,5-Bis-trifluoromethyl-pyridin-2-yl-(2H-pyrazole-3,4-diamine |
| 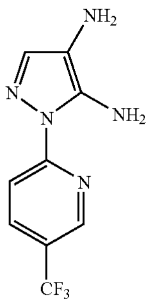 | 2-(5-Trifluoromethyl-pyridin-2-yl)-2H-pyrazole-3,4-diamine | 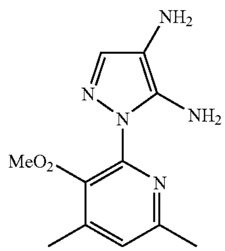 | 2-(3-Trifluoromethyl-pyridin-2-yl)-2H-pyrazole-3,4-diamine | 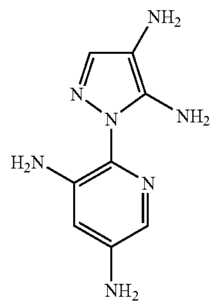 | 2-(4,5-Diamino-pyrazol-1-yl)-pyridine-3,5-diamine |
| 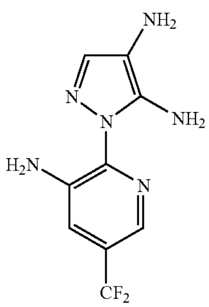 | 2-(3-Amino-5-trifluoromethylpyridin-2-yl)-2H-pyrazole-3,4-diamine | 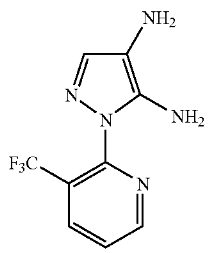 | 2-(3-Trifluoromethyl-pyridin-2-yl)-2H-pyrazole-3,4-diamine | 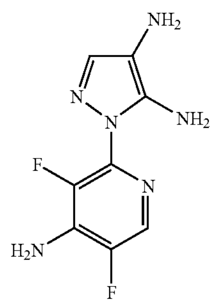 | 2-(4-Amino-3,5-difluoro-pyridin-2-yl)-2H-3,4-diamine |
| 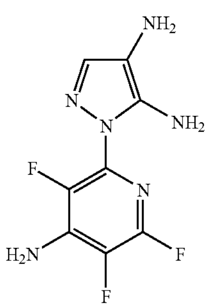 | 2-(4-Amino-3,5,6-trifluoro-pyridin-2-yl)-2H-pyrazole-3,4-diamine | 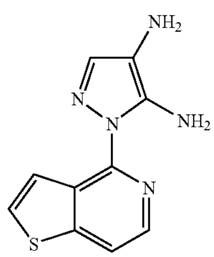 | 2-Thieno[3,2-C]pyridin-4-yl-2H-pyrazole-3,4-diamine | 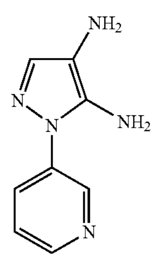 | 2-Pyridin-3-yl-2H-pyrazole-3,4-diamine |
| 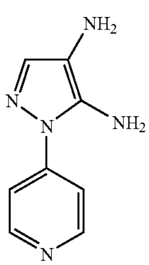 | 2-Pyridin-4-yl-2H-pyrazole-3,4-diamine | 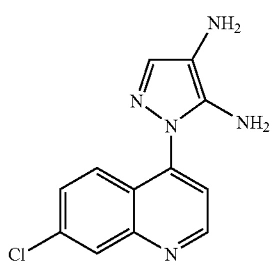 | 2-(7-Chloro-quinolin-4-yl)-2H-pyrazole-3,4-diamine | 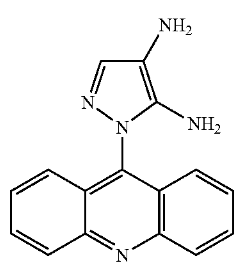 | 2-Acridin-9-yl-2H-pyrazole-3,4-diamine |

-continued

| Structure | Name | Structure | Name | Structure | Name |
|---|---|---|---|---|---|
| 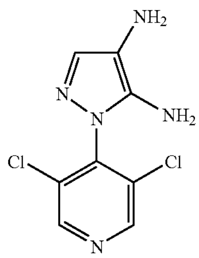 | 2-(3,5-Dichloro-pyridin-4-yl)-2H-pyrazole-3,4-diamine | 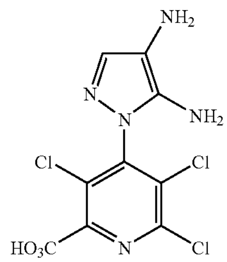 | 3,5,6-Trichloro-4-(4,5-diamino-pyrazol-1 yl)-pyridine-2-carboxylic acid | 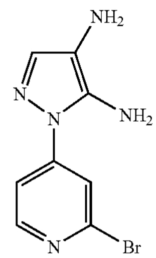 | 2-(2-Bromo-pyridin-4-yl)-2H-pyrazole-3,4-diamine |
| 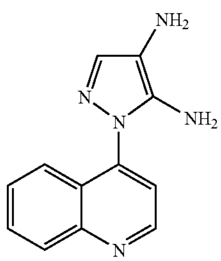 | 2-Quinolin-4-yl-2H-pyrazole-3,4-diamine | 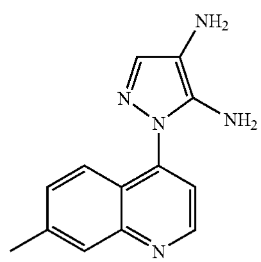 | 2-(7-Methyl-quinolin-4-yl)-2H-pyrazole-3,4-diamine | 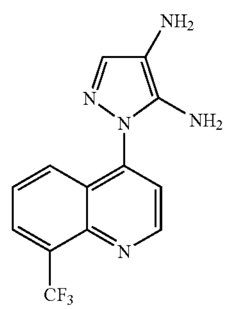 | 2-(8-Trifluoro methyl-quinolin-4-yl)-2H-pyrazole-3,4-diamine |
| 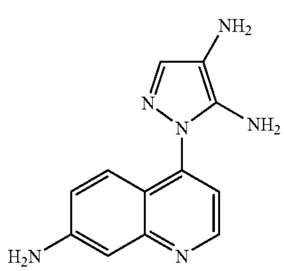 | 2-(7-Amino-quinolin-4-yl)-2H-pyrazole-3,4-diamine | 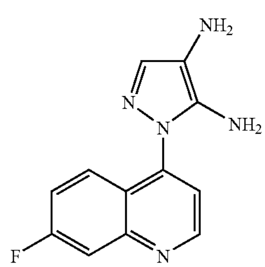 | 2-(7-Fluoro-quinolin-4-yl)-2H-pyrazole-3,4 diamine | 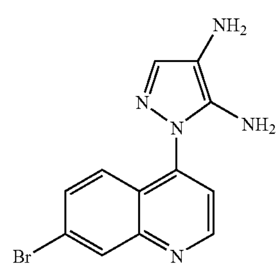 | 2-(7-BVromo-quinolin-4-yl)-2H-pyrazole-3,4-diamine |
| 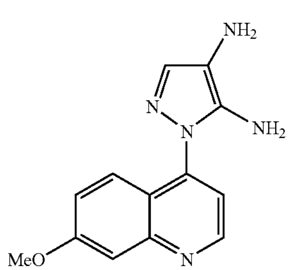 | 2-(7-Methoxy-quinolin-4-yl)-2H-pyrazole-3,4-diamine | 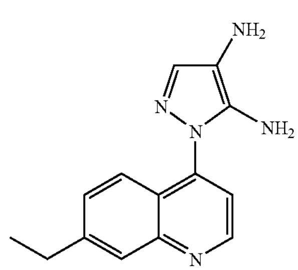 | 2-(7-Ethyl-quinolin-4-yl)-2H-pyrazole-3,4-diamine | 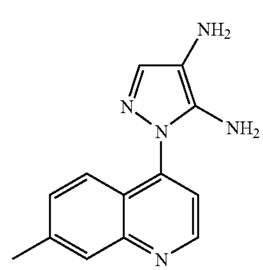 | 2-(7-Methyl-quinolin-4-yl)-2H-pyrazole-3,4-diamine |

-continued

| Structure | Name | Structure | Name | Structure | Name |
|---|---|---|---|---|---|
| (structure) | 2-(2-6-Dimethyl-quinolin-4-yl)-2H-pyrazole-3,4-diamine | (structure) | 2-(8-Isopropyl-2-methyl-quinolin-4-yl)-2H-pyrazole-3,4-diamine | (structure) | 2-(2,6,8-Trimethyl-quinolin-4-yl)-2H-pyrazole-3,4-diamine |
| (structure) | 2-(5-Chloro-8-methoxy-2-methyl-quinolin-4-yl)-2H-pyraxole-3,4-diamine | (structure) | 2-(3-methyane sulfonyl-pyridin-4-yl)-2H-pyrazole-3,4-diamine | | |

2) Pyrazine Series

| Structure | Name | Structure | Name | Structure | Name |
|---|---|---|---|---|---|
| (structure) | 2-Pyrazin-2-yl-2H-pyrazole-3,4-diamine | (structure) | 2-Quinoxalin-2-yl-2H-pyrazole-3,4-diamine | (structure) | 2-(3,7-Dichloro-quinoxalin-2-yl)-2H-pyrazole-3,4-diamine |
| (structure) | 2-(5-Chloro-3,6-diphenyl-pyrazin-2-yl)-2H-pyrazole-3,4-diamine | (structure) | 2-(3-Trifluoromethyl quinoxalin-2-yl)-2H-pyrazole-3,4-diamine | | |

3) Pyrazole Series

| Structure | Name |
|---|---|
| 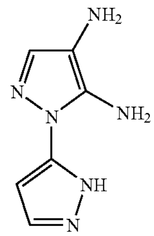 | 2'H-[1,3']Bipyrazolyl-4,5-diamine |
| 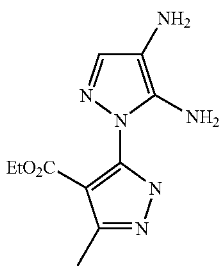 | 4,5-Diamino-5'-methyl-2'H-[1,3']bipyrazolyl-4'-carboxylic acid ethyl ester |
| 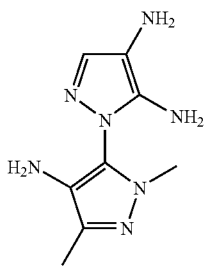 | 2',5'-Dimethyl-2'H-[1,3']bipyrazolyl-4,5,4'-triamine |

-continued

| Structure | Name |
|---|---|
| 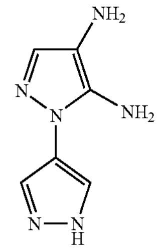 | 1'H-[1,4']Bipyrazolyl-4,5-diamine |
| 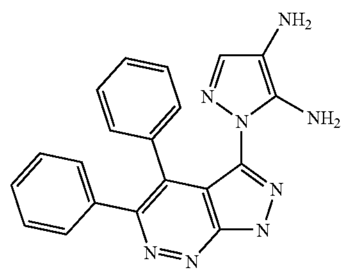 | 2-(4,5-Diphenyl-1H-pyrazolo[3,4-c]pyridazin-3-yl)-2H-pyrazole-3,4-diamine |

4) Pyrimidine Series

| Structure | Name | Structure | Name | Structure | Name |
|---|---|---|---|---|---|
| 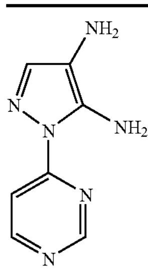 | 2-Pyrimidin-4-yl-2H-pyrazole-3,4-diamine | 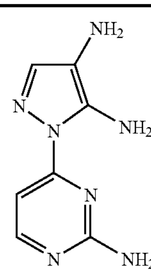 | 2-(2-Aminopyrimidin-4-yl)-2H-pyrazole-3,4-diamine | 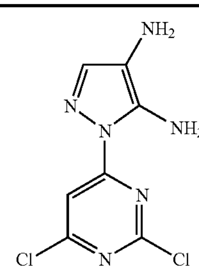 | 2-(2,6-Dichloropyrimindin-4-yl)-2H-pyrazole-3,4-diamine |
| 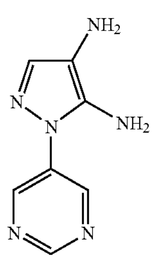 | 2-Pyrimidin-5-yl-2H-pyrazole-3,4-diamine | 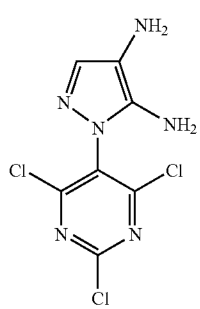 | 2-(2,4,6-Trichloropyrimidin-5-yl)-2H-pyrazole-3,4-diamine | 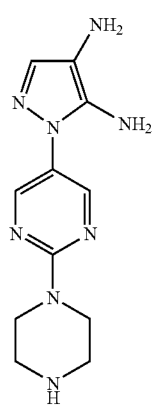 | 2-(2-Piperazin-1-yl-pyrimidin-5-yl)-2H-pyrazole-3,4-diamine |

5) Furan Series:

| Structure | Name | Structure | Name | Structure | Name |
|---|---|---|---|---|---|
| 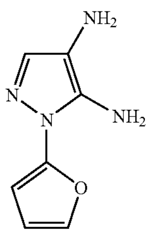 | 2-Furan-2-yl-2H-pyrazole-3,4-diamine | 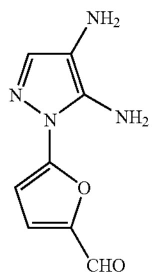 | 5-(4,5-Diamino-pyrazol-1-yl)-furan-2-carbaldehyde | 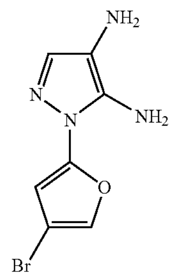 | 2-(4-Bromo-furan-2-yl)-2H-pyrazole-3,4-diamine |
| 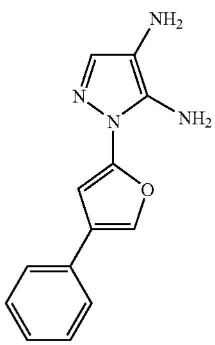 | 2-(4-Phenyl-furan-2-yl)-2H-pyrazole-3,4-diamine | 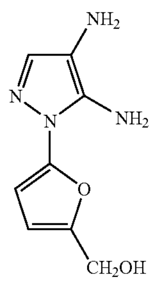 | 5-[(4,5-Diamino-pyrazol-1-yl)-furan-2-yl]-methanol | 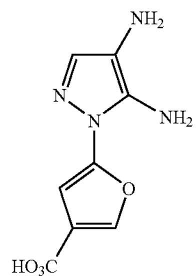 | 5-(4,5-Diamino-pyrazol-1-yl)furan-3-carboxylic acid |
| 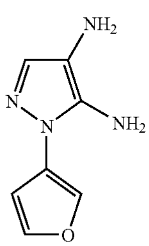 | 3-(4,5-Diamino-pyraxol-1-yl)furan | 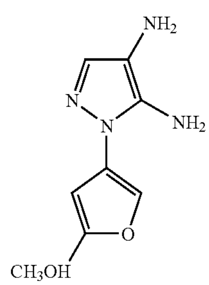 | 5-(4,5-Diamino-pyrazol-1-yl)-5H furan-2-one | | |

6) Thiophene Series:

| Structure | Name | Structure | Name | Structure | Name |
|---|---|---|---|---|---|
| 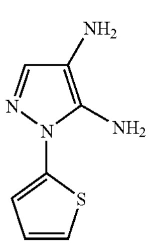 | 2-Thiophen 2-yl-2H-pyrazole-3,4-diamine | 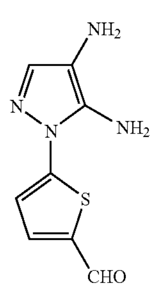 | 5-(4,5-Diamino pyrazol-1-yl)-thiophene-2-carbaldehyde | 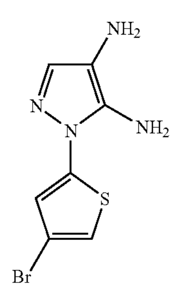 | 2-(4-Bromo-thiophen-2-yl)-2H-pyrazole-3,4-diamine |

-continued

| Structure | Name | Structure | Name | Structure | Name |
|---|---|---|---|---|---|
| 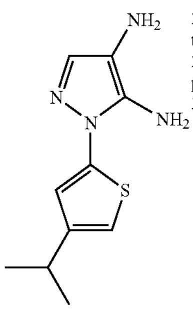 | 2-(4-Isopropyl thiophen 2-yl-2H-pyrazole-3,4-diamine | 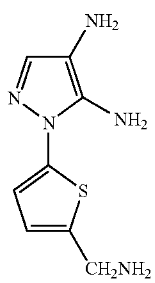 | 2-(5-Aminoethyl-thiophen-2-yl)-2H-pyrazole-3,4-diamine | 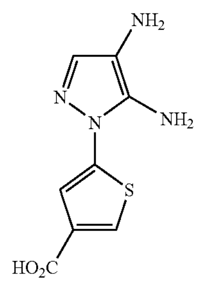 | 5-(4,5-Diamino pyrazol-1-yl)-thiophene-3-carboxylic acid |
| 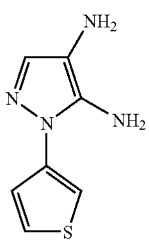 | 2-Thiophen 2-yl-2H-pyrazole-3,4-diamine | 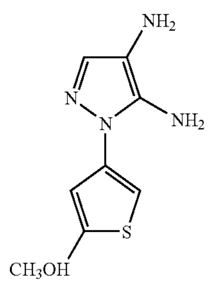 | [5-(4,5-Diamino pyrazol-1-yl)-thiophen-3-yl] methanol | | |

7) Triazole Series:

| Structure | Name | Structure | Name | Structure | Name |
|---|---|---|---|---|---|
| 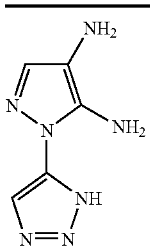 | 2-(3H-[1,2,3]Triazol-4-yl)-2H-pyrazole-3,4-diamine | 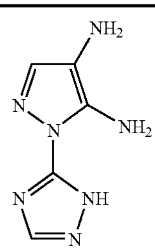 | 2-(2H-[1,2,3]Triazol-3-yl)-2H-pyrazole-3,4-diamine | 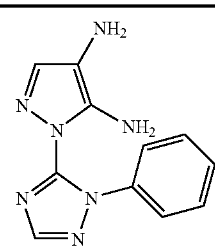 | 2-(2-Phenyl-2H-[1,2,3]triazol-3-yl)-2H-pyrazole-3,4-diamine |

8) Triazine Series:

| Structure | Name | Structure | Name | Structure | Name |
|---|---|---|---|---|---|
| 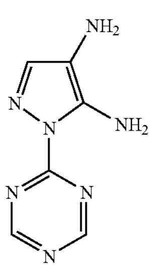 | 2-[1,3,5]Triazin-2-yl-2H-pyrazole-3,4 diamine | 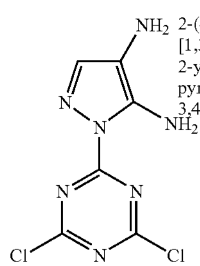 | 2-(4,6-Dichloro-[1,3,5]triazin-2-yl)-2H-pyrazole-3,4 diamine | 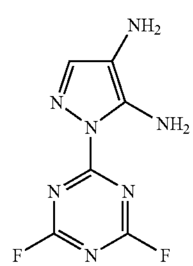 | 2-(4,6-Difluoro-[1,3,5]triazin-2-yl)-2H-pyrazole-3,4 diamine |

9) Pyrrole, Imidazole and Pyridazine Series

| Structure | Name | Structure | Name | Structure | Name |
|---|---|---|---|---|---|
| 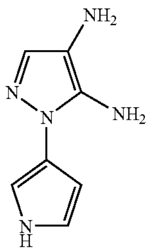 | 2-(1H-Pyrrol-3-yl)-2H-pyrazole-3,4-diamine | 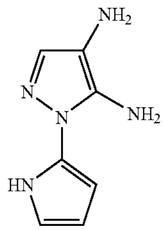 | 2-(1H-Pyrrol-2-yl)-2H-pyrazole-3,4-diamine | 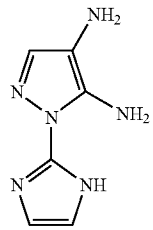 | 2-(1H-Imidazol-2-yl)-2H-pyrazole-3,4-diamine |
| 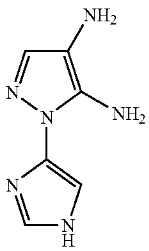 | 2-(1H-Pyrrol-4-yl)-2H-pyrazole-3,4-diamine | 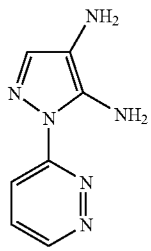 | 2-Pyridazin-3-yl)-2H-pyrazole-3,4-diamine | 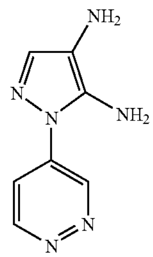 | 2-Pyridazin-4-yl)-2H-pyrazole-3,4-diamine |

The diaminopyrazoles of formula (I) that are preferred according to the invention have the following structures:

| Structure | Name | Structure | Name | Structure | Name |
|---|---|---|---|---|---|
| 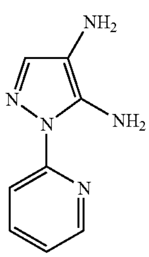 | 2-Pyridin-2-yl-2H-pyrazole-3,4-diamine | 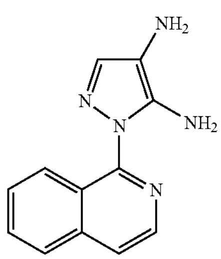 | 2-Isoquinolin-1-yl-2H-pyrazole-3,4-diamine | 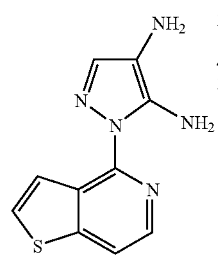 | 2-Thieno[3,2-c]pyridin-4-yl-2H-pyrazole-3,4 diamine |
| 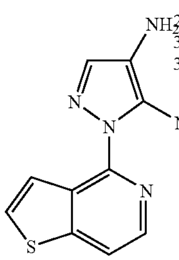 | 2-Pyridin-3-yl-2H-pyrazole-3,4-diamine | 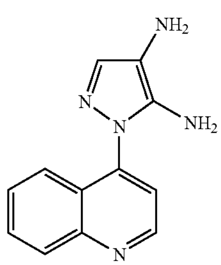 | 2-Quinolin-4-yl-2H-pyrazole-3,4-diamine | 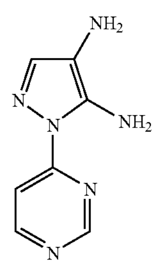 | 2-Pyrazin-2-yl-2H-pyrazole-3,4-diamine |
| 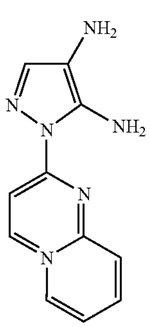 | 2-Quinoxalin-2-yl-2H-pyrazole-3,4-diamine | 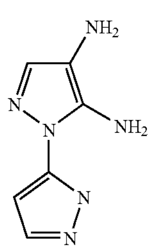 | 2'H-[1,3'] Bipyrazolyl-4,5-diamine | 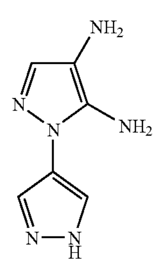 | 1'H-[1,4'] Bipyrazolyl-4,5-diamine |

-continued

| Structure | Name | Structure | Name | Structure | Name |
|---|---|---|---|---|---|
| 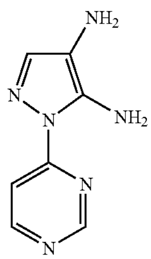 | 2-Pyrimidin-4-yl-2H-pyrazole-3,4-diamine | 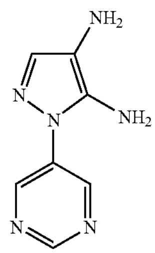 | 2-Pyrimidin-5-yl-2H-pyrazole-3,4-diamine | 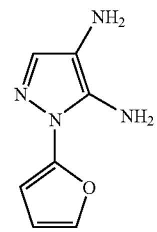 | 2-Puran-2-yl-2H-pyrazole-3,4-diamine |
| 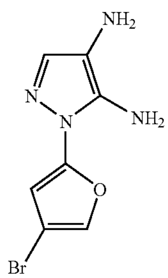 | 2-(4-Bromo-furan-2-yl)-2H-pyrazole-3,4-diamine | 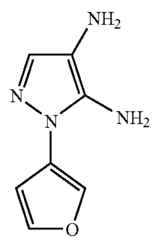 | 3-(4,5-Diamino-pyraxol-1-yl)-furan | 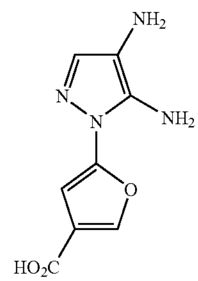 | 5-(4,5-Diamino-pyraxol-1-yl)-furan-3-carboxylic acid |
| 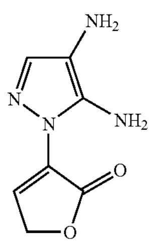 | 3-(4,5-Diamino-pyraxol-1-yl)-5H-furan-2-one | 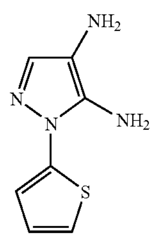 | 2-Thiophen-2-yl-2H-pyrazole-3,4-diamine | 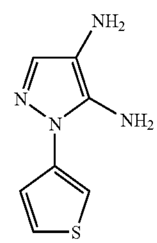 | 2-Thiophen-3-yl-2H-pyrazole-3,4-diamine |
| 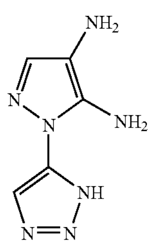 | 2-3H-[1,2,3]Triazol-4-yl)-2H-pyrazole-3,4-diamine | 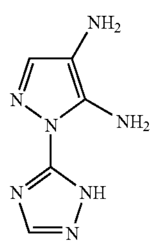 | 2-2H-[1,2,4]Triazol-3-yl)-2H-pyrazole-3,4-diamine | 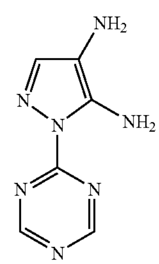 | 2-[1,3,5]Triazin-2-yl)-2H-pyrazole-3,4-diamine |
| 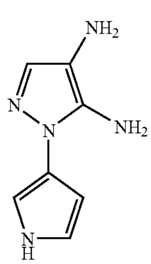 | 2-(1H-Pyrrol-3-yl)-2H-pyrazole-3,4-diamine | 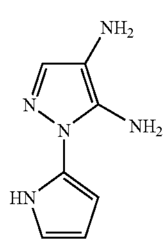 | 2-(1H-Pyrrol-2-yl)-2H-pyrazole-3,4-diamine | 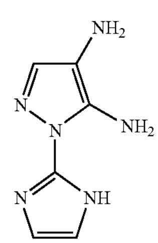 | 2-(1H-Imidazol-2-yl)-2H-pyrazole-3,4-diamine |

| Structure | Name | Structure | Name | Structure | Name |
|---|---|---|---|---|---|
| (structure) | 2-(1H-Imidizol-4-yl)-2H-pyrazole-3,4-diamine | (structure) | 2-Pyridazin-3-yl-2H-pyrazole-3,4-diamine | (structure) | 2-Pyridazin-2-yl-2H-pyrazole-3,4-diamine |

The diaminopyrazoles of formula (I) that are more particularly preferred according to the invention are 2-pyridin-2-yl-2H-pyrazole-3,4-diamine, 2-pyridin-3-yl-2H-pyrazole-3,4-diamine, 2-pyridin-4-yl-2H-pyrazole-3,4-diamine, 2-pyrazin-2-yl-2H-pyrazole-3,4-diamine, 2'H-[1,3']bipyrazolyl-4,5-diamine, 1'H-[1,4']bipyrazolyl-4,5-diamine, 2-pyrimidin-4-yl-2H-pyrazole-3,4-diamine, 2-pyrimidin-5-yl-2H-pyrazole-3,4-diamine, 2-furan-2-yl-2H-pyrazole-3,4-diamine, 3-(4,5-diaminopyrazol-1-yl)furan, 2-thiophen-2-yl-2H-pyrazole-3,4-diamine, 2-thiophen-2-yl-2H-pyrazole-3,4-diamine, 2-(3H-[1,2,3]triazol-4-yl)-2H-pyrazole-3,4-diamine, 2-(2H-[1,2,4]triazol-3-yl)-2H-pyrazole-3,4-diamine, 2-[1,3,5]triazin-2-yl-2H-pyrazole-3,4-diamine, 2-(1H-pyrrol-3-yl)-2H-pyrazole-3,4-diamine, 2-(1H-pyrrol-2-yl)-2H-pyrazole-3,4-diamine or the addition salts thereof with physiologically acceptable acids.

The diaminopyrazoles of formula (I) according to the invention are prepared, for example, according to the following general preparation method:

Synthetic Scheme:

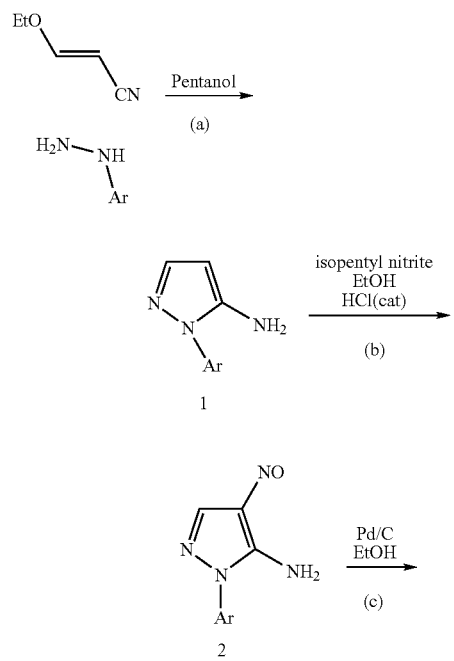

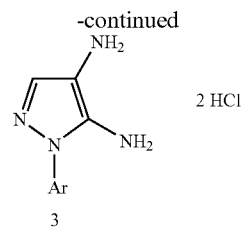

(a): selective cyclization
(b): selective nitrosation
(c): reduction

The operating conditions used will depend on the radical Ar of the reactant chosen.

The dye composition according to the invention especially contains from 0.001% to 10% by weight, preferably from 0.05% to 6% by weight and even more preferably from 0.1% to 3% by weight of at least one diaminopyrazole of formula (I) or of the salts thereof.

The dye composition in accordance with the invention may also contain, in addition to the diaminopyrazole(s) defined above, at least one additional oxidation base that may be chosen from the oxidation bases conventionally used in oxidation dyeing and among which mention may be made especially of para-phenylenediamines, bis(phenyl)alkylenediamines, para-aminophenols, ortho-aminophenols and heterocyclic bases other than the diaminopyrazoles used in accordance with the invention.

Among the para-phenylenediamines that may be mentioned more particularly, for example, are para-phenylenediamine, para-tolylenediamine, 2,6-dimethyl-para-phenylenediamine, 2-β-hydroxyethyl-para-phenylenediamine, 2-n-propyl-para-phenylenediamine, 2-isopropyl-para-phenylenediamine, N-(β-hydroxypropyl)-para-phenylenediamine, N,N-bis(β-hydroxyethyl)-para-phenylenediamine, 4-amino-N-(β-methoxyethyl)aniline and the para-phenylenediamines described in French patent application FR 2 630 438, and the addition salts thereof.

Among the bis(phenylalkylenediamines that may be mentioned more particularly, for example, are N,N'-bis-(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis-(4-methylaminophenyl)tetramethylenediamine and N,N'-bis (ethyl)-N,N'-bis(4'-amino-3'-methylphenyl)ethylenediamine, and the addition salts thereof.

Among the para-aminophenols that may be mentioned more particularly, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof.

Among the ortho-aminophenols that may be mentioned more particularly, for example, are 2-aminophenol, 2-amino-5-methylphenol, 2-amino-6-methylphenol and 5-acetamido-2-aminophenol, and the addition salts thereof.

Among the heterocyclic bases that may be mentioned more particularly, for example, are pyridine derivatives, pyrimidine derivatives, pyrazole derivatives other than the diaminopyrazoles of formula (I) used in accordance with the invention, and the addition salts thereof.

When they are used, these additional oxidation bases preferably represent from 0.0005% to 12% by weight relative to the total weight of the dye composition and even more preferably from 0.005% to 6% by weight relative this weight.

The oxidation dye compositions in accordance with the invention may also contain at least one coupler and/or at least one direct dye, especially to modify the shades or to enrich them with glints.

The couplers that may be used in the oxidation dye compositions in accordance with the invention may be chosen from the couplers conventionally used in oxidation dyeing, and among which mention may be made especially of meta-phenylenediamines, meta-aminophenols, meta-diphenols, mono- or polyhydroxylated naphthalene derivatives and heterocyclic couplers such as, for example, indole or pyridine derivatives, and the addition salts thereof with an acid.

These couplers are chosen more particularly from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureido-aniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis-(β-hydroxyethylamino)toluene, and the addition salts thereof.

When they are present, these couplers especially represent from 0.0001% to 10% of the total weight of the dye composition, preferably from 0.005% to 5% by weight and even more preferably from 0.1% to 3% of this weight.

In general, the addition salts with an acid that may be used in the context of the dye compositions of the invention (oxidation bases and couplers) are chosen especially from the hydrochlorides, hydrobromides, sulfates, tartrates, lactates and acetates.

The medium that is suitable for dyeing (or support) used according to the invention consists of water or of a mixture of water and at least one organic solvent chosen from $C_1$–$C_4$ lower alkanols, polyols and polyol ethers, aromatic alcohols, similar products and mixtures thereof.

The dye composition according to the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, reducing agents, sunscreens, penetrating agents, sequestering agents, fragrances, buffers, dispersants, conditioners, for instance silicones, film-forming agents, preserving agents and opacifiers.

The pH of the dye composition according to the invention is between 3 and 12.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The dye composition according to the invention may be in various forms, such as in the form of liquids, creams or gels, or in any other form that is suitable for dyeing keratin fibers, and especially human hair.

Another subject of the invention is a process for dyeing keratin fibers, and in particular human keratin fibers such as the hair, using the dye composition as defined above.

According to this process, at least one dye composition as defined above is applied to the fibers, for a time that is sufficient to develop the desired coloration, either in air or using an oxidizing agent. The dye composition may optionally contain oxidation catalysts, so as to accelerate the oxidation process.

According to a first embodiment of the process of the invention, the coloration of the fibers may be performed without adding an oxidizing agent, solely by contact with atmospheric oxygen.

According to a second embodiment of the process of the invention, at least one dye composition as defined above is applied to the fibers, the color being revealed at acidic, neutral or alkaline pH using an oxidizing agent that is added to the composition just at the time of use, or which is present in an oxidizing composition applied simultaneously or sequentially in a separate manner.

According to this second embodiment of the dyeing process of the invention, the dye composition described above is preferably mixed, at the time of use, with an oxidizing composition containing, in a medium that is suitable for dyeing, at least one oxidizing agent present in an amount that is sufficient to develop a coloration. The mixture obtained is than applied to the keratin fibers and is left for an action time of 3 to 50 minutes and preferably 5 to 30 minutes, after which the fibers are rinsed, washed with shampoo, rinsed again and dried.

The oxidizing agent present in the oxidizing composition as defined above may be chosen from the oxidizing agents conventionally used for the oxidation dyeing of keratin fibers, and among which mention may be made of hydrogen peroxide, urea peroxide, alkali metal bromates and persalts such as perborates and persulfates. Hydrogen peroxide is particularly preferred.

The pH of the oxidizing composition containing the oxidizing agent as defined above is such that, after mixing with the dye composition, the pH of the resulting composition applied to the keratin fibers preferably ranges between 3 and 12, and even more preferably between 5 and 11. It is adjusted to the desired value by means of acidifying or basifying agents usually used in the dyeing of keratin fibers, and as defined above.

The oxidizing composition as defined above may also contain various adjuvants conventionally used in compositions for dyeing the hair and as defined above.

The composition that is finally applied to the keratin fibers may be in various forms, such as in the form of liquids, creams or gels, or in any other form that is suitable for dyeing keratin fibers, and especially human hair.

Another subject of the invention is a multi-compartment device or dyeing "kit" or any other multi-compartment packaging system, a first compartment of which contains the dye composition as defined above, and a second compartment of which contains the oxidizing composition as defined above. These devices may be equipped with a means for applying the desired mixture to the hair, such as the devices described in patent FR-2 586 913 in the name of the Applicant.

The examples that follow are intended to illustrate the invention without, however, limiting its scope.

EXAMPLES

Example of the synthesis of 2-pyridin-2-yl-2H-pyrazole-3,4-diamine hydrochloride

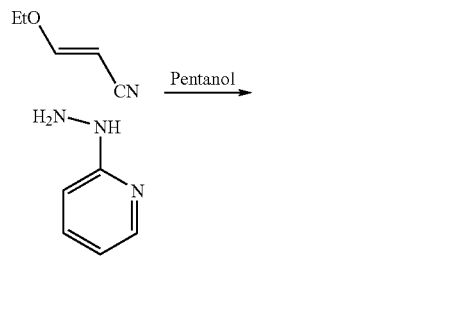

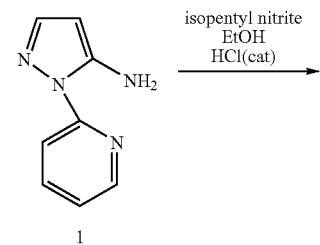

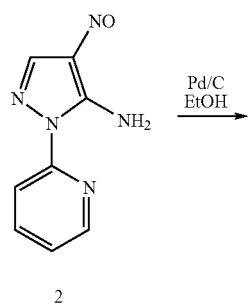

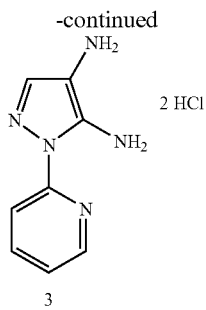

Synthesis of 2-pyridin-2-yl-2H-pyrazol-3-ylamine (1):

A solution of 2-hydrazinopyridine (38.9 g, 453 mmol) was slowly added to a solution of 3-ethoxyacrylonitrile (31.5 g, 324 mmol) in pentanol (155 ml). The reaction mixture was brought to reflux for 5 h. 2-Hydrazinopyridine (10.6 g, 97 mmol) was again added and the reaction was allowed to continue to reflux for 4 h. The progress of the reaction is observed by TLC and, when the reaction is complete, the mixture is concentrated under reduced pressure until the excess hydrazinopyridine has precipitated. The filtrate was purified by column chromatography to give 2-pyridin-2-yl-2H-pyrazol-3-ylamine in the form of a white solid (2.75 g, 5.3%).

$^1$H NMR (400 MHz, $d_6$-DMSO):

8.40 (1H, m, $H_{pyridine}$), 7.93 (1H, m, $H_{pyridine}$), 7.86 (1H, m, $H_{pyridine}$), 7.36 (1H, J=2 Hz, $H_{pyrazole}$), 7.23 (1H, m, $H_{pyridine}$), 6.78 (2H, $S_{broad}$), $NH_2$), 5.42 (1H, J=2 Hz, $H_{pyrazole}$).

Elemental analysis: ($C_8H_8N_4$): found: C: 58.30%, H: 4.96%, N: 33.42%. theoretical: C: 59.99%, H: 5.03%, N: 34.98%.

Synthesis of 4-nitroso-2-pyridin-2-yl-2H-pyrazol-3-ylamine (2):

HCl (37%, 11 μl) was added to a heterogeneous solution of 2-pyridin-2-yl-2H-pyrazol-3-ylamine (2.2 g, 13.7 mmol) in absolute ethanol (15 ml). The reaction mixture was subsequently cooled to 0° C. and isopentyl nitrite (2.02 ml, 15 mmol) was slowly added. The reaction mixture became dark. After the isopentyl nitrite had been completely added, the reaction mixture was allowed to return to ambient temperature. After 2.5 h at ambient temperature, the reaction mixture was cooled to 5° C. and filtered. The solid was washed with absolute MeOH (10 ml) and was then triturated twice from heptane. The solid was dried under vacuum at 35° C. to give 4-nitroso-2-pyridin-2-yl-2H-pyrazol-3-ylamine (2.1 g, 81%) in the form of a green solid.

$^1$H NMR (400 MHz, $d_6$-DMSO): 9.21 (2H, s, $NH_2$), 8.97 (1H, s, $H_{pyrazole}$), 8.49 (1H, m, $H_{pyridine}$), 8.04 (1H, m, $H_{pyridine}$), 7.92 49 (1H, m, $H_{pyridine}$), 7.40 (1H, m, $H_{pyridine}$).

$^{13}$C NMR (400 MHz, $d_6$-DMSO): 152.5, 152.3, 147.2, 143.9, 139.7, 135.0, 121.3, 113.0.

Elemental analysis: ($C_8H_7N_5O$): found: C: 51.19%, H: 3.95%, N: 36.79%, O: 8.09%. theoretical: C: 50.79%, H: 3.73%, N: 37.02%, O: 8.46%.

Synthesis of 2-pyridin-2-yl-2H-pyrazole-3,4-diamine hydrochloride (3):

A mixture of 4-nitroso-2-pyridin-2-yl-2H-pyrazol-3-yl-amine (2.0 g, 10.5 mmol) in EtOH (130 ml) containing a 10% Pd/C catalyst (Engelhard, 50% moisture, 410 mg) was hydrogenated in an autoclave (250 ml) at 6 bar for 3.0 h. The catalyst was filtered off under an inert atmosphere and washed with EtOH (50 ml), and the filtrate was recovered in an ethanolic solution (50 ml) comprising hydrochloric acid (37%, 1.3 ml). The orange-colored solution is evaporated to dryness. The crude product is triturated twice from the minimum amount of EtOH (20 ml) to give the hydrochloride (1.84 eq HCl) of 2-pyridin-2-yl-2H-pyrazole-3,4-diamine (1.5 g, 59%) in the form of a light beige solid.

Elemental analysis: ($C_8H_9N_5 \cdot 1.77HCl$; MW=242.28 g/mol) found: C: 39.09%, H: 4.43%, N: 28.21%, Cl: 27.81%. theoretical: C: 40.08%, H: 4.53%, N: 29.21%, Cl: 26.17%.

$^1$H NMR (400 MHz, $d_6$-DMSO): 10.30 (2H, s, HCl), 8.64 (1H, m, $H_{pyridine}$), 8.24–8.05 (2H, m, $H_{pyridine}$), 7.77 (1H, s, $H_{pyrazole}$), 7.68–7.50 (5H, m, $NH_2$ and $H_{pyridine}$).

Examples of Dye Composition in Alkaline Medium

| The following composition is prepared: | |
| --- | --- |
| diaminopyrazole base of formula (I) | $5 \times 10^{-3}$ mol |
| coupler | $5 \times 10^{-3}$ mol |
| oleyl alcohol polyglycerolated with 2 mol of glycerol | 4.0 g |
| oleyl alcohol polyglycerolated with 4 mol of glycerol, containing 78% active material (A.M.) | 5.7 g A.M. |
| oleic acid | 3.0 g |
| oleylamine containing 2 mol of ethylene oxide, sold under the trade name Ethomeen O12 by the company Akzo | 7.0 g |
| diethylaminopropyl laurylamino succinamate, sodium salt, at 55% A.M. | 3.0 g A.M. |
| oleyl alcohol | 5.0 g |
| oleic acid diethanolamide | 12.0 g |
| propylene glycol | 3.5 g |
| ethyl alcohol | 7.0 g |
| dipropylene glycol | 0.5 g |
| propylene glycol monomethyl ether | 9.0 g |
| sodium metabisulfite as an aqueous solution containing 35% A.M. | 0.455 g A.M. |
| ammonium acetate | 0.8 g |
| antioxidant, sequestering agent | qs |
| fragrance, preserving agent | qs |
| aqueous ammonia containing 20% $NH_3$ | 100 g | pH = 9.5
A.M. means "active material"

The base and the coupler are as defined below.

| DYEINGS AT ALKALINE pH | | |
| --- | --- | --- |
| Examples | Base | Coupler |
| 1 | 2-pyridin-2-yl-2H-pyrazole-3,4-diamine | m-aminophenol |
| 2 | 2-pyridin-2-yl-2H-pyrazole-3,4-diamine | 6-chloro-2-methyl-5-aminophenol |
| 3 | 2-pyridin-2-yl-2H-pyrazole-3,4-diamine | 2,4-diamino-1-(β-hydroxyethyloxy)-benzene dihydrochloride |

-continued

| DYEINGS AT ALKALINE pH | | |
| --- | --- | --- |
| Examples | Base | Coupler |
| 4 | 2-pyridin-2-yl-2H-pyrazole-3,4-diamine | 2-methyl-5-aminophenol |

At the time of use, each dye composition is mixed, weight for weight, with a 20-volumes aqueous hydrogen peroxide solution (6% by weight), the pH of which has been adjusted to about 2.5 with orthophosphoric acid.

The mixture is applied to natural gray hair containing 90% white hairs, at a rate of 5 g per 0.5 g of hair.

After 30 minutes, the hair is rinsed, washed with a standard shampoo, rinsed again and dried.

The color of the locks was evaluated in the L*a*b* system, on white and permanent-waved hair, using a Minolta CM 2002 spectrophotometer.

In the L*a*b* space, the lightness is indicated by the value L* on a scale from 0 to 100, while the chromatic data is expressed by a* and b* which indicate two color axes, a* the red-green axis and b* the yellow-blue axis.

According to this system, the higher the value of L, the paler and less intense the color. Conversely, the lower the value of L, the darker or more intense the color.

| | White hair | | |
| --- | --- | --- | --- |
| Examples | L* | a* | b* |
| Example 1 | 32.1 | 21.4 | 6.18 |
| Example 2 | 41.8 | 24.2 | 19.0 |
| Example 3 | 29.2 | 20.9 | 5.4 |
| Example 4 | 43.9 | 20.4 | 22.43 |

The diaminopyrazoles according to the invention thus make it possible to obtain strong and chromatic shades at alkaline pH.

Example of Dyeing Composition in Neutral Medium

The same formulations as above are prepared, replacing the aqueous ammonia with citric acid in an amount such that the pH is equal to 7.

| DYEING AT NEUTRAL pH | | |
| --- | --- | --- |
| Example | Base | Coupler |
| 5 | 2-pyridin-2-yl-2H-pyrazole-3,4-diamine | 2-methyl-5-aminophenol |

Locks of natural gray hair containing 90% white hairs are dyed with the dye composition 5 above in the same manner as for the dyeing at alkaline pH.

The following shades are obtained:

| Example | Natural white hair | | |
|---------|------|------|------|
|         | L*   | a*   | b*   |
| Example 5 | 42.5 | 15.8 | 23.8 |

At neutral pH, the diaminopyrazoles according to the invention make it possible to obtain strong shades.

The invention claimed is:

1. A diaminopyrazole compound of formula (I):

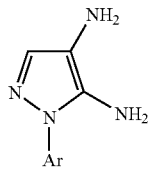

in which Ar is a pyridinyl, pyrazinyl, pyrimidinyl, pyridazinyl, pyrrolyl, imidazolyl, pyrazolyl, furanyl, thiophenyl, triazolyl, triazinyl, naphthyl, azanaphthyl, diazanaphthyl, triazanaphthyl, or tetraazanaphthyl radical or a physiologically acceptable salt thereof.

2. The compound of claim 1, wherein Ar is substituted by at least one radical chosen from linear or branched $C_1$ to $C_6$ alkyl radicals, linear or branched $C_1$ to $C_6$ alkoxy radicals, linear or branched $C_1$ to $C_6$ mono- or polyaminoalkyl radicals, linear or branched $C_1$ to $C_6$ mono- or polyhydroxyalkyl radicals, amino, hydroxyl, F, Cl, Br, I, trifluoromethyl, CHO, $CO_2H$, $CO_2Me$, $CO_2Et$, $CONH_2$, $CONHR_1$, $CON(R_1)_2$, $SO_3H$, $SO_2NH_2$, $SO_2Me$ or piperazinyl radicals, or phenyl radicals optionally substituted by at least one radical chosen from linear or branched $C_1$ to $C_6$ alkyl radicals, linear or branched $C_1$ to $C_6$ alkoxy radicals, linear or branched $C_1$ to $C_6$ mono- or polyaminoalkyl radicals, linear or branched $C_1$ to $C_6$ mono- or polyhydroxyalkyl radicals or amino, hydroxyl, F, Cl, Br, I, trifluoromethyl, CHO, $CO_2H$, $CO_2Me$, $CO_2Et$, $CONH_2$, $SO_3H$, $SO_2NH_2$, $SO_2N(R_1)_2$ or $SO_2Me$ radicals, $R_1$ being chosen from linear or branched $C_1$ to $C_6$ alkyl radicals, linear or branched $C_1$ to $C_6$ mono- or polyaminoalkyl radicals, linear or branched $C_1$ to $C_6$ mono- or polyhydroxyalkyl radicals, or trifluoromethyl, CHO, $CO_2Me$, $CO_2Et$, $CONH_2$, $SO_3H$, $SO_2NH_2$ or $SO_2Me$ radicals, or a physiologically acceptable salt of any of these.

3. The compound of claim 1, wherein the Ar radical is a quinolinyl, isoquinolinyl, oxyisoquinolinyl, quinoxalinyl or naphthyridinyl, acridinyl, pyrazolo[3,4-b]pyridinyl, pyrazolo[3,4-c]pyridazinyl, or thieno[3,2-c]pyridinyl radical.

4. The compound of claim 1, wherein the Ar radical is a pyridinyl radical.

5. The compound of claim 1, further defined as 2-pyridin-2-yl-2H-pyrazole-3,4-diamine, 2-isoquinolin-1-yl-2H-pyrazole-3,4-diamine, 2-(6-methyl-4-trifluoromethylpyridin-2-yl)-2H-pyrazole-3,4-diamine, 2-(6-chloro-4-trifluoromethylpyridin-2-yl)-2H-pyrazole-3,4-diamine, 2-(5-chloro-3,6-bistrifluoromethylpyridin-2-yl)-2H-pyrazole-3,4-diamine, 2-(1,3,4-trimethyl-1H-pyrazolo[3,4-b]pyridin-6-yl)-2H-pyrazole-3,4-diamine, 2-(3-aminopyridin-2-yl)-2H-pyrazole-3,4-diamine, 2-(5-aminopyridin-2-yl)-2H-pyrazole-3,4-diamine, 2-(5,7-bistrifluoromethyl[1,8]naphthyridin-2-yl)-2H-pyrazole-3,4-diamine, 2-(2-oxyisoquinolin-3-yl)-2H-pyrazole-3,4-diamine, 2-(3-amino-4-methyl-1H-pyrazolo[3,4-b]pyridin-6-yl)-2H-pyrazole-3,4-diamine, 2-(6-fluoropyridin-2-yl)-2H-pyrazole-3,4-diamine, 2-(4,6-bistrifluoromethylpyridin-2-yl)-2H-pyrazole-3,4-diamine, 2-(6-chloropyridin-2-yl)-2H-pyrazole-3,4-diamine, 2-(4,5-bistrifluoromethylpyridin-2-yl)-2H-pyrazole-3,4-diamine, 2-(5-trifluoromethylpyridin-2-yl)-2H-pyrazole-3,4-diamine, 2-(3-methanesulfonyl-4,6-dimethylpyridin-2-yl)-2H-pyrazole-3,4-diamine, 2-(4,5-diaminopyrazol-1-yl)pyridine-3,5-diamine, 2-(3-amino-5-trifluoromethylpyridin-2-yl)-2H-pyrazole-3,4-diamine, 2-(3-trifluoromethylpyridin-2-yl)-2H-pyrazole-3,4-diamine, 2-(4-amino-3,5-difluoropyridin-2-yl)-2H-pyrazole-3,4-diamine, 2-(4-amino-3,5,6-trifluoropyridin-2-yl)-2H-pyrazole-3,4-diamine, 2-thieno[3,2-c]pyridin-4-yl-2H-pyrazole-3,4-diamine, 2-pyridin-3-yl-2H-pyrazole-3,4-diamine, 2-pyridin-4-yl-2H-pyrazole-3,4-diamine, 2-(7-chloroquinolin-4-yl)-2H-pyrazole-3,4-diamine, 2-acridin-9-yl-2H-pyrazole-3,4-diamine, 2-(3,5-dichloropyridin-4-yl)-2H-pyrazole-3,4-diamine, 3,5,6-trichloro-4-(4,5-diaminopyrazol-1-yl)pyridine-2-carboxylic acid, 2-(2-bromopyridin-4-yl)-2H-pyrazole-3,4-diamine, 2-quinolin-4-yl-2H-pyrazole-3,4-diamine, 2-(7-methylquinolin-4-yl)-2H-pyrazole-3,4-diamine, 2-(8-trifluoromethylquinolin-4-yl)-2H-pyrazole-3,4-diamine, 2-(7-aminoquinolin-4-yl)-2H-pyrazole-3,4-diamine, 2-(7-fluoroquinolin-4-yl)-2H-pyrazole-3,4-diamine, 2-(7-bromoquinolin-4-yl)-2H-pyrazole-3,4-diamine, 2-(7-methoxyquinolin-4-yl)-2H-pyrazole-3,4-diamine, 2-(7-ethylquinolin-4-yl)-2H-pyrazole-3,4-diamine, 2-(7-methylquinolin-4-yl)-2H-pyrazole-3,4-diamine, 2-(2,6-dimethylquinolin-4-yl)-2H-pyrazole-3,4-diamine, 2-(8-isopropyl-2-methylquinolin-4-yl)-2H-pyrazole-3,4-diamine, 2-(2,6,8-trimethylquinolin-4-yl)-2H-pyrazole-3,4-diamine, 2-(5-chloro-8-methoxy-2-methylquinolin-4-yl)-2H-pyrazole-3,4-diamine, 2-(3-methanesulfonylpyridin-4-yl)-2H-pyrazole-3,4-diamine, 2-pyrazin-2-yl-2H-pyrazole-3,4-diamine, 2-quinoxalin-2-yl-2H-pyrazole-3,4-diamine, 2-(3,7-dichloroquinoxalin-2-yl)-2H-pyrazole-3,4-diamine, 2-(5-chloro-3,6-diphenylpyrazin-2-yl)-2H-pyrazole-3,4-diamine, 2-(3-trifluoromethylquinoxalin-2-yl)-2H-pyrazole-3,4-diamine, 2'H-[1,3']bipyrazolyl-4,5-diamine, 2',5'-dimethyl-2'H-[1,3']bipyrazolyl-4,5,4'-triamine, 2-(4,5-diphenyl-1H-pyrazolo[3,4-c]pyridazin-3-yl)-2H-pyrazole-3,4-diamine, ethyl ester of 4,5-diamino-5'-methyl-2'H-[1,3']bipyrazolyl-4'-carboxylic acid, 1'H-[1,4']bipyrazolyl-4,5-diamine, 2-pyrimidin-4-yl-2H-pyrazole-3,4-diamine, 2-(2-aminopyrimidin-4-yl)-2H-pyrazole-3,4-diamine, 2-(2,6-dichloropyrimidin-4-yl)-2H-pyrazole-3,4-diamine, 2-pyrimidin-5-yl-2H-pyrazole-3,4-diamine, 2-(2,4,6-trichloropyrimidin-5-yl)-2H-pyrazole-3,4-diamine, 2-(2-piperazin-1-yl-pyrimidin-5-yl)-2H-pyrazole-3,4-diamine, 2-furan-2-yl-2H-pyrazole-3,4-diamine, 5-(4,5-diaminopyrazol-1-yl)-furan-2-carbaldehyde, 2-(4-bromofuran-2-yl)-2H-pyrazole-3,4-diamine, 2-(4-phenylfuran-2-yl)-2H-pyrazole-3,4-diamine, [5-(4,5-diaminopyrazol-1-yl)-furan-2-yl]methanol, 5-(4,5-diaminopyrazol-1-yl)-furan-3-carboxylic acid, 3-(4,5-diaminopyrazol-1-yl)furan, [5-(4,5-diaminopyrazol-1-yl)-furan-3-yl]methanol, 3-(4,5-diaminopyrazol-1-yl)-5H-furan-2-one, 2-thiophen-2-yl-2H-pyrazole-3,4-diamine, 5-(4,5-diaminopyrazol-1-yl)thiophene-2-carbaldehyde, 2-(4-bromothiophen-2-yl)-2H-pyrazole-3,4-diamine, 2-(4-isopropylthiophen-2-yl)-2H-pyrazole-3,4-diamine, 2-(5-aminomethylthiophen-2-yl)-2H-pyrazole-3,4-diamine, 5-(4,5-diaminopyrazol-1-yl)thiophene-3-carboxylic acid, 2-thiophen-3-yl-2H-pyrazole-3,4-diamine, [5-(4,5-diaminopyrazol-1-yl)thiophen-3-yl]methanol, 2-(3H-[1,2,3]triazol-4-yl)-2H-pyrazole-3,4-diamine, 2-(2H-

[1,2,4]triazol-3-yl)-2H-pyrazole-3,4-diamine, 2-(2-phenyl-2H-[1,2,4]triazol-3-yl)-2H-pyrazole-3,4-diamine, 2-[1,3,5]triazin-2-yl-2H-pyrazole-3,4-diamine, 2-(4,6-dichloro[1,3,5]triazin-2-yl)-2H-pyrazole-3,4-diamine, 2-(4,6-difluoro[1,3,5]triazin-2-yl)-2H-pyrazole-3,4-diamine, 2-(1H-pyrrol-3-yl)-2H-pyrazole-3,4-diamine, 2-(1H-pyrrol-2-yl)-2H-pyrazole-3,4-diamine, 2-(1H-imidazol-2-yl)-2H-pyrazole-3,4-diamine, 2-(1H-imidazol-4-yl)-2H-pyrazole-3,4-diamine, 2-pyridazin-3-yl-2H-pyrazole-3,4-diamine, 2-pyridazin-4-yl-2H-pyrazole-3,4-diamine or a physiologically acceptable acid salt of any of these.

6. The compound of claim 1, further defined as 2-pyridin-2-yl-2H-pyrazole-3,4-diamine, 2-isoquinolin-1-yl-2H-pyrazole-3,4-diamine, 2-thieno[3,2-c]pyridin-4-yl-2H-pyrazole-3,4-diamine, 2-pyridin-3-yl-2H-pyrazole-3,4-diamine, 2-quinolin-4-yl-2H-pyrazole-3,4-diamine, 2-pyrazin-2-yl-2H-pyrazole-3,4-diamine, 2-quinoxalin-2-yl-2H-pyrazole-3,4-diamine, 2'H-[1,3']bipyrazolyl-4,5-diamine, 1'H-[1,4']bipyrazolyl-4,5-diamine, 2-pyrimidin-4-yl-2H-pyrazole-3,4-diamine, 2-pyrimidin-5-yl-2H-pyrazole-3,4-diamine, 2-furan-2-yl-2H-pyrazole-3,4-diamine, 2-(4-bromofuran-2-yl)-2H-pyrazole-3,4-diamine, 3-(4,5-diaminopyrazol-1-yl)furan, 5-(4,5-diaminopyrazol-1-yl)furan-3-carboxylic acid, 3-(4,5-diaminopyrazol-1-yl)-5H-furan-2-one, 2-thiophen-2-yl-2H-pyrazole-3,4-diamine, 2-thiophen-3-yl-2H-pyrazole-3,4-diamine, 2-(3H-[1,2,3]triazol-4-yl)-2H-pyrazole-3,4-diamine, 2-(2H-[1,2,4]triazol-3-yl)-2H-pyrazole-3,4-diamine, 2-[1,3,5]triazin-2-yl-2H-pyrazole-3,4-diamine, 2-(1H-pyrrol-3-yl)-2H-pyrazole-3,4-diamine, 2-(1H-pyrrol-2-yl)-2H-pyrazole-3,4-diamine, 2-(1H-imidazol-2-yl)-2H-pyrazole-3,4-diamine, 2-(1H-imidazol-4-yl)-2H-pyrazole-3,4-diamine, 2-pyridazin-3-yl-2H-pyrazole-3,4-diamine, 2-pyridazin-4-yl-2H-pyrazole-3,4-diamine or a physiologically acceptable acid salt of any of these.

7. The compound of claim 1, further defined as a physiologically acceptable hydrochloride, hybromide, sulfate, tartrate, lactate, or acetate acid salt.

8. A composition for the oxidation dyeing of keratin fibers comprising at least one diaminopyrazole of formula (I):

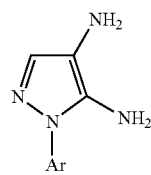

(I)

in which Ar is a 5- or 6-membered heteroaromatic radical which can be condensed with one or more aromatic or heteroaromatic rings, each comprising 5 or 6 ring members, or a physiologically acceptable salt thereof, in a medium suitable for dyeing.

9. The composition of claim 8, further defined as comprising from 0.001% to 10% by weight of at least one diaminopyrazole of formula (I) or salt thereof.

10. The composition of claim 8, wherein the medium that is suitable for dyeing comprises water or of a mixture of water and at least one organic solvent further defined as a $C_1$–$C_4$ lower alkanol, polyol, polyol ether, or aromatic alcohol, or mixtures thereof.

11. The composition of claim 8, further defined as having a pH of between 3 and 12.

12. The composition of claim 8, comprising at least one additional oxidation base further defined as a para-phenylenediamine, bis(phenyl)alkylenediamine, para-aminophenol, ortho-aminophenol, or heterocyclic base other than the diaminopyrazole of formula (I), or an addition salt of one of these with an acid.

13. The composition of claim 12, wherein the additional oxidation base comprises from 0.0005% to 12% by weight relative to the total weight of the dye composition.

14. The composition of claim 8, further defined as comprising at least one direct dye.

15. The composition of claim 8, further defined as comprising at least one coupler.

16. The composition of claim 15, wherein the coupler is a meta-phenylenediamine, meta-aminophenol, meta-diphenol, monohydroxylated naphthalene derivative, polyhydroxylated naphthalene derivative, or heterocyclic coupler, or an addition salt of one of these with an acid.

17. The composition of claim 15, wherein the coupler represents from 0.0001% to 10% by weight relative to the total weight of the dye composition.

18. The composition of claim 8, further defined as comprising at least one direct dye and at least one coupler.

19. A process for dyeing keratin fibers, comprising applying to the fibers a composition comprising, as an oxidation base, at least one diaminopyrazole of formula (I):

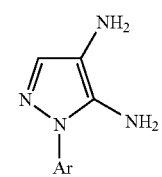

(I)

in which Ar is a 5- or 6-membered heteroaromatic radical which can be condensed with one or more aromatic or heteroaromatic rings, each comprising 5 or 6 ring members, or a physiologically acceptable salt thereof, in a medium suitable for dying, for a time that is sufficient to develop the desired coloration, either in air or using an oxidizing agent.

20. The process of claim 19, wherein the keratin fibers are further defined as human hair.

21. The process of claim 19, further comprising applying an oxidation catalyst to the fibers.

22. The process of claim 19, wherein no oxidizing agent is applied and coloration is revealed by contact with atmospheric oxygen.

23. The process of claim 19, further comprising an application of an oxidizing agent to the fibers.

24. The process of claim 23, wherein the oxidizing agent is added to the dye composition prior to application of the dye composition to the fibers.

25. The process of claim 23, wherein the oxidizing agent is comprised in an oxidizing composition that is applied to the fibers simultaneously or sequentially with regard to the dyeing composition.

26. The process of claim 23, wherein the oxidizing agent is hydrogen peroxide, urea peroxide, an alkali metal bromate, or a persalt.

27. A kit comprising:
   a first compartment containing a composition comprising a diaminopyrazole of formula (I):

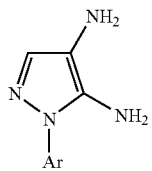

(I)

in which Ar is a 5- or 6-membered heteroaromatic radical which can be condensed with one or more aromatic or heteroaromatic rings, each comprising 5 or 6 ring members, or a physiologically acceptable salt thereof, in a medium suitable for dying; and
   a second compartment containing an oxidizing composition.

28. A composition for the oxidation dyeing of keratin fibers comprising from 0.001% to 10% by weight of at least one diaminopyrazole of formula (I):

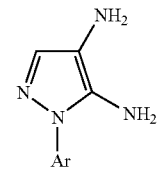

(I)

in which Ar is a 5- or 6-membered heteroaromatic radical which can be condensed with one or more aromatic or heteroaromatic rings, each comprising 5 or 6 ring members, or a physiologically acceptable salt thereof, in a medium suitable for dyeing.

29. A process for dyeing human hair, comprising applying to the hair a composition comprising, as an oxidation base, at least one diaminopyrazole of formula (I):

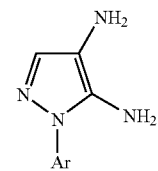

(I)

in which Ar is a 5- or 6-membered heteroaromatic radical which can be condensed with one or more aromatic or heteroaromatic rings, each comprising 5 or 6 ring members, or a physiologically acceptable salt thereof, in a medium suitable for dying, for a time that is sufficient to develop the desired coloration, either in air or using an oxidizing agent.

* * * * *